United States Patent [19]
Fusauchi et al.

[11] Patent Number: 5,821,348
[45] Date of Patent: Oct. 13, 1998

[54] PROCESS FOR PRODUCING ETOPOSIDE

[75] Inventors: Yukihiro Fusauchi, Maebashi; Hiroshi Yoshikawa, Fujioka, both of Japan

[73] Assignee: Nippon Kayaku Kabushiki Kaisha, Tokyo, Japan

[21] Appl. No.: 760,647

[22] Filed: Dec. 4, 1996

[30] Foreign Application Priority Data

Dec. 4, 1995 [JP] Japan .................................. 7-337720
Dec. 8, 1995 [JP] Japan .................................. 7-345114

[51] Int. Cl.$^6$ ...................................................... C07H 1/00
[52] U.S. Cl. ........................ 536/18.6; 536/18.1; 536/18.5
[58] Field of Search ................. 536/18.1, 18.5, 536/18.6

[56] References Cited

FOREIGN PATENT DOCUMENTS

| | | |
|---|---|---|
| 0 394 908 | 10/1980 | European Pat. Off. . |
| 0 162 701 | 8/1989 | European Pat. Off. . |
| 0 401 800 | 6/1990 | European Pat. Off. . |
| 0 394 907 | 10/1990 | European Pat. Off. . |
| 0 652 226 | 11/1994 | European Pat. Off. . |
| 93/02094 | 2/1993 | WIPO . |

*Primary Examiner*—Elli Peselev
*Attorney, Agent, or Firm*—Nields, Lemack & Dingman

[57] ABSTRACT

A protected 4'-demethyl-4-epipodophyllotoxin is reacted with a protected glucose derivative in a non-halogen type organic solvent in a 0.1–7-fold parts by volume based on 1 part by weight of the protected 4'-demethyl-4-epipodophyllotoxin to give an etoposide derivative of formula (3) which is protected at its functional groups:

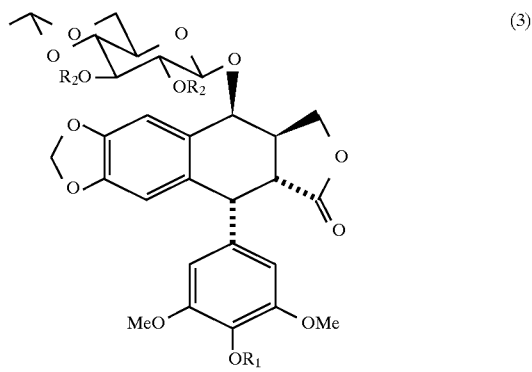

wherein each of $R_1$ and $R_2$ each is a protective group for hydroxy, if necessary, followed by removal of these protective groups. By use of the non-halogen type organic solvent in lieu of any harmful halogen type solvent, formation of undesirable by-products can be minimized so that the etoposides can be obtained in a high yield and high purity.

14 Claims, No Drawings

PROCESS FOR PRODUCING ETOPOSIDE

BACKGROUND OF THE INVENTION

1. Field of the Invention

The present invention relates to a process for producing 4'-demethyl-4-epipodophyllotoxin-β-D-ethylideneglucoside (hereinafter referred to as etoposide), which has been widely used as an anticancer agent, and a derivative thereof wherein the functional group(s) of etoposide are protected.

2. Related Art Statement

EP 0394908A1 and EP 0162701B1 disclose a process for producing etoposide with protected functional group(s) of formula (3)

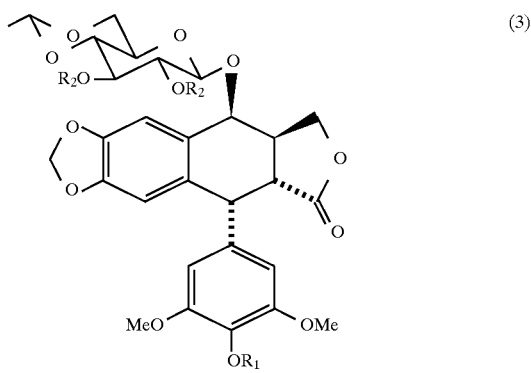

wherein each of $R_1$ and $R_2$ is a protective group for hydroxy, which comprises reacting a protected 4'-demethyl-4-epipodophyllotoxin of formula (1)

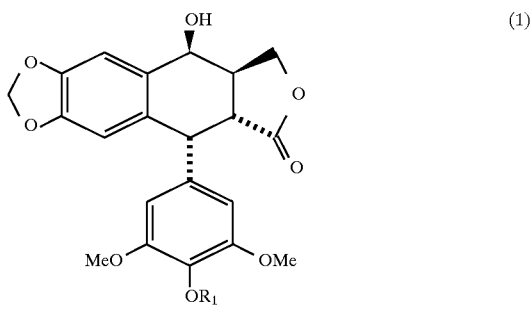

wherein $R_1$ is as defined above, with a protected glucose derivatives of formula (2)

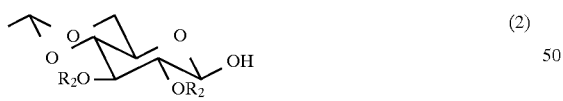

wherein $R_2$ is as defined above, in the presence of a boron trifluoride dialkyl ether complex as a catalyst. In the reaction, a halogen type solvent such as dichloromethane or chloroform is employed as a preferable solvent for the reaction. EP 0394907A1 discloses that the reaction may also be carried out in a solvent other than dichloromethane, for example, ethyl acetate, ether, acetone, acetonitrile or the like. However, only dichloroethane is employed at working examples in EP 0394907A1.

In recent years, it has been usually desired to use in a chemical reaction non-halogen type solvents in place of halogen type ones due to the risk of causing cancer in human and adverse affect against environment. Despite such a desire, any known reactions for producing etoposide or derivative thereof do not actually use non-halogen type solvents in the reaction, since the reaction encounters problems that the catalyst used in the reaction is inactivated, the starting compound or reaction product is adversely affected by non-halogen type solvents and these solvents have a poor solubility. In addition, the present inventors' investigations reveal that when the reaction is carried out in a non-halogen type solvent at the same amount as that of a halogen type solvent conventionally used, a dimer of the protected 4'-demethyl-4-epipodophyllotoxin of formula (1) and α-glucoside of the etoposide of formula (3) are by-produced in extremely large quantities, together with the desired β-glucoside of the etoposide of formula (3). The by-produced dimer and the α-glucoside reduce the yield of the desired product as well as the quality of the produced etoposides. It is thus desired to minimize the formation of these by-products as less as possible.

SUMMARY OF THE INVENTION

The present inventors have extensively investigated the reaction under various conditions in a non-halogen type solvent instead of a conventional halogen type solvent. As a result, it has been found that when an amount of the non-halogen type solvent, especially an amount of non-halogen type aliphatic solvent is reduced to not more than the half of an amount of halogen type solvent conventionally used for the reaction, formation of the dimer of protected 4'-demethyl-4-epipodophyllotoxin can be markedly prevented. It has also been found that when a non-halogen type aliphatic solvent and a non-halogen type aromatic solvent are employed in the reaction as a solvent mixture, the mixture is excellent as a reaction solvent for preventing the formation of the dimer. It has further been found that the co-presence of an ether in the reaction system can markedly prevent formation of the undesired α-glucoside. The present invention has come to be accomplished based on these findings.

That is, a first aspect of the present invention is to provide a process for producing an etoposide or derivative thereof which comprises reacting a protected 4'-demethyl-4-epipodophyllotoxin of formula (1):

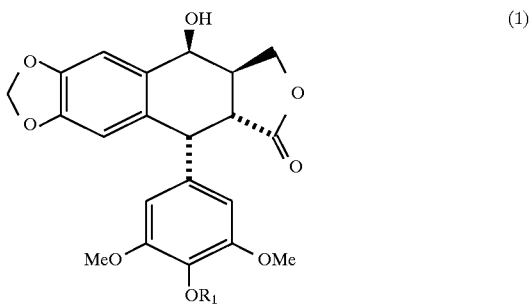

wherein $R_1$ is a protective group for hydroxy, with a protected glucose derivative of formula (2):

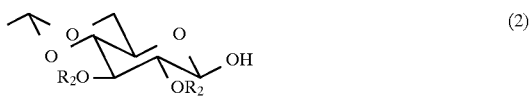

wherein $R_2$ is a protective group for hydroxy in a non-halogen type organic solvent, in the presence of a non-halogen type aliphatic solvent in a 0.1 to 7-fold part by volume based on 1 part by weight of the etoposide derivative of formula (1) and a dehydration condensing catalyst, to obtain a protected etoposide of formula (3):

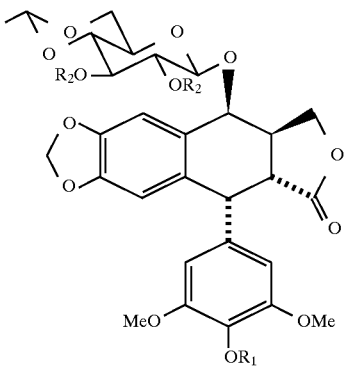

(3)

wherein $R_1$ and $R_2$ are as defined above, and optionally removing the protective group(s) from the protected etoposide.

A second aspect of the present invention is to provide a process for producing an etoposide or derivative thereof, wherein an ether is co-present in the reaction system.

A third aspect of the present invention is to provide a process for producing an etoposide or derivative thereof, wherein a boron trifluoride di-lower alkyl ether complex or a tri($C_1$—$C_4$ alkyl)silyltrifluoro-methanesulfonate is employed as the catalyst.

A fourth aspect of the present invention is to provide a process for producing an etoposide or derivative thereof, wherein the ether is a mono or polyether containing 1 to 5 ether groups and 2 to 6 linear or cyclic hydrocarbon groups having 1 to 6 carbon atoms.

A fifth aspect of the present invention is to provide a process for producing an etoposide or derivative thereof, wherein the mono or polyether is represented by formula (4):

$$R_3\text{—O—}(R_4\text{—O})_n\text{—}R_5 \qquad (4)$$

wherein n is an integer of 0 to 4; each of $R_3$ and $R_5$ independently is an alkyl group having 1 to 4 carbon atoms; and $R_4$ is a linear or branched alkylene group having 2 to 4 carbon atoms.

A sixth aspect of the present invention is to provide a process for producing an etoposide or derivative thereof, wherein as the non-halogen type solvent, acetonitrile alone or a solvent mixture of acetonitrile and an aromatic solvent is employed.

A seventh aspect of the present invention is to provide a process for producing an etoposide or derivative thereof which comprises reacting a protected 4'-demethyl-4-epipodophyllotoxin of (1):

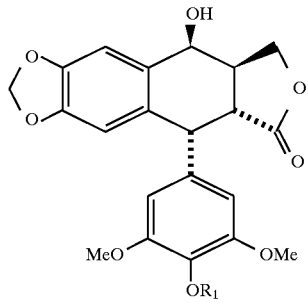

(1)

wherein $R_1$ is a protective group for hydroxy, with a protected glucose derivative of formula (2):

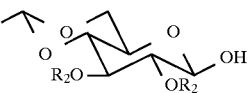

(2)

wherein $R_2$ is a protective group for hydroxy, in a solvent mixture of a non-halogen type aliphatic solvent and a non-halogen type aromatic solvent in the presence of a dehydration condensing catalyst, to obtain a protected etoposide of formula (3):

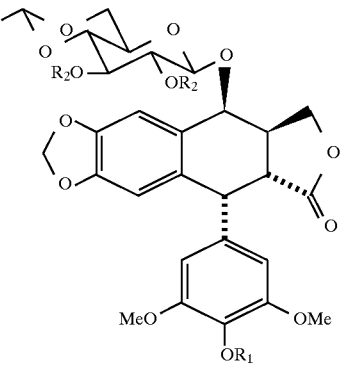

(3)

wherein $R_1$ and $R_2$ are as defined above or hydrogen atom, and optionally removing the protective group(s) from the protected etoposide.

An eighth aspect of the present invention is to provide a process for producing an etoposide or derivative thereof, wherein the non-halogen type aliphatic solvent is preferably an aliphatic polar solvent, and is more preferably selected from the group consisting of a nitrile compound, a ketone compound and an ester compound.

A ninth aspect of the present invention is to provide a process for producing an etoposide or derivative thereof, wherein used is as the non-halogen type aliphatic solvent a nitrile compound of which aliphatic hydrocarbon group is selected from the group consisting of an alkyl group having 1 to 3 carbon atoms and an alkylene group having 1 to 3 carbon atoms; a ketone compound of which aliphatic hydrocarbon groups at the both sides therein are selected from the group consisting of an alkyl group having 1 to 5 carbon atoms and an alkylene group having 1 to 5 carbon atoms; and an ester compound which is an ester of acetic acid or propionic acid and an alcohol having 1 to 4 carbon atoms.

A tenth aspect of the present invention is to provide a process for producing an etoposide or derivative thereof, wherein the non-halogen type aromatic solvent is benzene or a benzene substituted with 1 to 3 substituents selected from the group consisting of an alkyl group having 1 to 4 carbon atoms and nitro.

An eleventh aspect of the present invention is to provide a process for producing an etoposide or derivative thereof, wherein an amount of the non-halogen type aliphatic solvent used is in the range of 0.1 to 4-fold parts by volume based on 1 part by weight of the compound of formula (1) and the total amount of the solvent mixture is in the range of 1 to 10-fold parts by volume based on 1 part by weight of the compound of formula (1).

A twelfth aspect of the present invention is to provide a process for producing an etoposide or derivative thereof, wherein the non-halogen type aliphatic solvent is selected from the group consisting of acetonitrile, propionitrile, acetone, methyl ethyl ketone, methyl isobutyl ketone, ethyl acetate and isopropyl acetate; the non-halogen type aromatic solvent is selected from the group consisting of benzene, toluene, xylene, ethylbenzene, nitrobenzene and nitrotoluene; and the dehydration condensing catalyst is a boron trifluoride di-alkyl ether having 1 to 4 carbon atoms and is employed in an amount ranging from 1 to 15 equivalents to the 4'-demethyl-4-etoposide of formula (1).

A thirteenth aspect of the present invention is to provide a process for producing an etoposide or derivative thereof, wherein the non-halogen type aliphatic solvent is a solvent mixture of acetonitrile and benzene, toluene or xylene, an amount of acetonitrile used being in the range of 0.3 to 3 parts by volume based on 1 part by weight of the compound of formula (1), a total amount of the solvent mixture being in the range of 2 to 6 parts by volume based on 1 part by weight of the compound of formula (1), and an amount of the boron trifluoride di-alkyl ether having 1 to 4 carbon atoms used as a catalyst is in the range of 1 to 6 equivalents to the compound of formula (1).

A fourteenth aspect of the present invention is to provide a process for producing an etoposide or derivative thereof which comprises reacting a protected 4'-demethyl-4-epipodophyllotoxin of formula (1) with a protected glucose derivative of formula (2) in a non-halogen type aliphatic solvent in the presence of a dehydration condensing catalyst to obtain a protected etoposide of formula (3), and optionally removing the protective group(s) from the protected etoposide, wherein the non-halogen type aliphatic solvent is a nitrile compound at an amount in the range of 1 to 10-fold parts by volume based on 1 part by weight of the compound of formula (1).

A fifteenth aspect of the present invention is to provide an etoposide, which contains not greater than 50 ppb halogen compounds.

A sixteenth aspect of the present invention is to provide an etoposide, which is substantially free of a dimer of 4'-demethyl-4-epipodophyllotoxin.

A seventeenth aspect of the present invention is to provide an etoposide, which is substantially free of etoposide in the α-glucoside form.

DESCRIPTION OF THE PREFERRED EMBODIMENTS

Representative examples of the protective group $R_1$ for hydroxy in the protected 4'-demethyl-4-epipodophyllotoxin of formula (1) are preferably acyl groups having 1 to 10 carbon atoms, for example, a lower $C_1$—$C_6$ alkylcarbonyl group, a lower $C_1$—$C_6$ alkyloxycarbonyl group, benzoyl, benzyloxycarbonyl, a lower $C_1$—$C_6$ alkylcarbonyl group substituted with 1 to 3 halogen atoms, a lower $C_1$—$C_6$ alkyloxy-carbonyl group substituted with 1 to 3 halogen atoms, a benzoyl group substituted with 1 to 3 halogen atoms, and a benzyloxycarbonyl group substituted with 1 to 3 halogen atoms. Of these protective groups, an acetyl or an acetyl group substituted with 1 to 3 halogen atoms is preferred, wherein specific examples of the halogen atom are fluorine, chlorine and bromine. Monochloroacetyl and dichloroacetyl are particularly preferred as the protective group. As the protective group $R_2$ for hydroxy in the protected glucose derivative of formula (2), the protective groups for $R_1$ described above can be employed, for example, a lower alkylcarbonyl group, benzoyl, a lower $C_1$—$C_6$ alkyloxycarbon group substituted with 1 to 3 halogen atoms, a lower $C_1$—$C_6$ alkylcarbonyl group substituted with 1 to 3 halogen atoms, a benzoyl group substituted with 1 to 3 halogen atoms, and a lower $C_1$—$C_6$ alkyloxycarbonyl group substituted with 1 to 3 halogen atoms. Of these protective groups, an acetyl or an acetyl group substituted with 1 to 3 halogen atoms is preferred, wherein specific examples of the halogen atom are fluorine, chlorine and bromine. Monochloroacetyl and dichloroacetyl are particularly preferred as the protective group.

As the solvent, a non-halogen type organic solvent is employed in the reaction described above. A non-halogen type aliphatic solvent and a non-halogen type aromatic solvent are preferable as the non-halogen type organic solvent, and employed singly or as admixture thereof. A preferred non-halogen type aliphatic solvent includes non-halogen type aliphatic polar solvent such as nitrile, ketone, ether compounds and preferred are ones having 1 to 10 carbon atoms. As the nitrile compound, preferably employed may be those having an alkyl or alkylene moiety of 1 to 3 carbon atoms in the aliphatic hydrocarbon group. Specific examples of such nitrile compounds are acetonitrile, propionitrile, butyronitrile and acrylonitrile. As the ketone compound, preferably employed may be those having aliphatic hydrocarbon groups at the both sides of the ketone compound which contains an alkyl or alkylene moiety having 1 to 5 carbon atoms. Specific examples of the ketone compound include acetone, methyl ethyl ketone, methyl propyl ketone (2-pentanone), 3-pentanone, methyl isobutyl ketone (2-hexanone), 3-hexanone, methyl vinyl ketone and ethyl vinyl ketone and the like. As the ester compound, any ester compound may be employed without any particular limitation, so long as it can be used as a solvent. Preferred are esters of acetic acid or propionic acid and an alcohol having 1 to 4 carbon atoms. Specific examples of the ester compound are ethyl acetate, n-propyl acetate, isopropyl acetate, n-butyl acetate, t-butyl acetate, methyl propionate, ethyl propionate, n-propyl propionate, 2-propyl propionate and butyl propionate and the like. As the non-halogen type aromatic solvent, preferably there are benzene and a benzene substituted with 1 to 3 substituents selected from the group consisting of an alkyl group having 1 to 4 carbon atoms and nitro. Specific examples of the non-halogen type aromatic solvent include benzene, toluene, xylene, ethylbenzene, propylbenzenes, butylbenzenes, xylene, trimethylbenzenes, nitrobenzene and nitrotoluenes.

In the solvent system described above, a solvent mixture of the non-halogen type aliphatic and aromatic solvents are advantageously employed for the reaction above. Representative examples of the preferred combination are mixtures of the non-halogen type aliphatic solvent selected from the group consisting of acetonitrile, propionitrile, acetone, methyl ethyl ketone, methyl isobutyl ketone, ethyl acetate and isopropyl acetate; and the non-halogen type aromatic solvent selected from the group consisting of benzene, toluene, xylene, ethylbenzene, nitrobenzene and nitrotoluene. A more preferred combination of the two solvents is acetonitrile selected from the non-halogen type aliphatic solvent and toluene selected from the non-halogen type aromatic solvent.

The amount of the solvent is preferably 0.1 to 7 parts by volume, more preferably 2 to 6 parts by volume based on 1 part by weight of the compound of formula (1). Where a mixture of the non-halogen type aliphatic and aromatic solvents is employed, the total amount may exceed the upper limit given above. However, it is preferred to keep the non-halogen type aliphatic solvent in an amount within the range shown above. Accordingly, the non-halogen type aliphatic solvent is contained in the range of preferably 0.1 to 4-fold parts by volume, more preferably 0.3 to 3-fold parts by volume, based on 1 part by weight of the compound of formula (1).

Where the nitrile type solvent such as acetonitrile is employed, the solvent may be in the range of approximately 1 to 10-fold parts by volume based on 1 part by weight of the compound of formula (1).

Representative examples of dehydration condensing catalyst include a complex of boron trifluoride and dialkyl ether or tri($C_1$—$C_4$) alkylsilyl trifluoro methane sulfonate. The alkyl moiety of the complex of boron trifluoride and dialkyl ether have preferably 1 to 4 carbon atoms. A preferred example of the dialkyl ether is diethyl ether. For the purpose for functioning as a catalyst, for example, the complex is used in the range of generally 1 to 15-fold equivalents, preferably 1 to 10-fold equivalents, more preferably 1 to 6-fold equivalents to the compound of formula (1).

When an ether is present in the reaction system, the reaction proceeds advantageously, since formation of the undesired α-glucoside form can be minimized. In this case, the ether is preferably a mono or polyether containing 1 to 5 ether groups and 2 to 6 linear or cyclic hydrocarbon groups having 1 to 6 carbon atoms. More preferably, the mono or polyether is represented by formula (4):

$$R_3—O—(R_4—O)_n—R_5 \qquad (4)$$

wherein n is an integer of 0 to 4; each of $R_3$ and $R_5$ independently is an alkyl group having 1 to 4 carbon atoms; and $R_4$ is a linear or branched alkylene group having 2 to 4 carbon atoms.

As the linear hydrocarbon groups having 1 to 6 carbon atoms which are located at both sides of the ether compound molecule, a lower alkyl group such as methyl, ethyl or propyl is preferred. As the linear hydrocarbon group having 1 to 6 carbon atoms which is located in the middle of the ether compound molecule, a lower alkylene group which may optionally be branched is preferred. Specific examples of the lower alkylene group are methylene, ethylene and 1-methylethylene. Examples of the cyclic hydrocarbon group include phenyl and phenylene.

Representative examples of the ether compound of formula (4) include dimethyl ether, diethyl ether and dipropyl ether of each of ethylene glycol, propylene glycol, diethylene glycol and triethylene glycol. Particularly preferred are ethylene glycol dimethyl ether, ethylene glycol diethyl ether and diethylene glycol dimethyl ether. Among them, ethylene glycol dimethyl ether is more preferred as the ether compound. An mount of the ether compound used may vary depending upon an amount of the catalyst used and an amount of the solvent used, but may be generally in the range of 1 to 50%, preferably 10 to 30% based on the solvent.

Each of the compounds of formulas (1) and (2) is generally employed for the reaction wherein the compound of formula (2) is used in an amount ranging from 1 to 5 equivalents, preferably 1.2 to 3 equivalents to the compound of formula (1).

This reaction is carried out generally at a low temperature below 10° C., preferably under cooling at 0° to −30° C., more preferably at −5° to −20° C. The reaction system is kept in an anhydrous state as possible as one can. A drying agent such as molecular sieve, etc. may be employed, if necessary and desired.

Depending upon necessity, the protective group(s) may be removed from the reaction product of formula (3) obtained in the reaction described above. The protective group(s) can be readily removed by ordinary methods, for example, solvolysis such as hydrolysis, alcoholysis and the like, or reduction reaction using palladium catalyst and the like. Especially, where the protective group is an acyl group, it may be removed by heating the reaction product of formula (3) in methanol or a non-halogen type solvent mixture containing methanol in the presence of a conventional deacylation catalyst such as various acetates or basic substances such as pyridine.

The crude etoposide obtained by the reaction above may be purified by recrystallization once or twice from, or by suspension once or twice in a non-halogen type solvent, e.g., a lower alcohol such as methanol, a lower ketone such as acetone, a lower carboxylic acid ester such as ethyl acetate, an ethereal solvent such as isopropyl ether, a hydrocarbon solvent such as hexane or a solvent mixture thereof.

According to the process of the present invention, the halogen compound content in the purified etoposide can be reduced to 80 ppb or less, preferably 50 ppb or less, more preferably several ppb to about 30 ppb, by means of high performance chromatography. Etoposide conventional synthesized using a halogen type solvent unavoidably contains more than hundred and several tens ppm halogen compounds such as halogen type solvents, etc., whereas the halogen compound content of the etoposide derivative obtained by the process of the present invention is dramatically reduced sufficiently to distinguish the same over the prior art etoposide. Herein the halogen compound content is used to mean that when two or more halogen compounds are present in the system, the content is expressed in total of all the halogen compounds.

The thus purified etoposide substantially contains neither dimer of the starting 4'-demethyl-4-epipodophyllotoxin nor α-glucoside form of etoposide. As an index for evaluation, the content of these undesired by-products is, for example, 1% or less, preferably 0.1% or less.

In the present invention, the compound of formula (1) and the compound of formula (2) prepared by any process can be used without any limitation, but it is preferred to use the compound of formula (1) and the compound of formula (2) synthesized without using any halogen type solvent.

Representative examples of the compound of formula (1) include the following:

(1) 4'-chloroacetyl-4'-demethyl-epipodophyllotoxin (in formula (1), $R_1$=—$COCH_2Cl$)
(2) 4'-bromoacetyl-4'-demethyl-epipodophyllotoxin (in formula (1), $R_1$=—$COCH_2Br$)
(3) 4'-dichloroacetyl-4'-demethyl-epipodophyllotoxin (in formula (1), $R_1$=—$COCHCl_2$)
(4) 4'-dibromoacetyl-4'-demethyl-epipodophyllotoxin (in formula (1), $R_1$=—$COCHBr_2$)
(5) 4'-trichloroacetyl-4'-demethyl-epipodophyllotoxin (in formula (1), $R_1$=—$COCCl_3$)
(6) 4'-tribromoacetyl-4'-demethyl-epipodophyllotoxin (in formula (1), $R_1$=—$COCBr_3$)
(7) 4'-β,β,β-trichloroethoxycarbonyl-4'-demethyl-epipodophyllotoxin (in formula (1), $R_1$=—$COOCH_2CCl_3$)
(8) 4'-β,β,β-tribromoethoxycarbonyl-4'-demethyl-epipodophyllotoxin (in formula (1), $R_1$=—$COOCH_2CBr_3$).

Representative examples of the compound shown by formula (2) include the following:

(1) 4,6-O-ethylidene-2,3-di-O-chloroacetyl-β-D-glucopyranose (in formula (2), $R_2$=—$COCH_2Cl$)
(2) 4,6-O-ethylidene-2,3-di-O-bromoacetyl-β-D-glucopyranos(in formula (2), $R_2$=—$COCH_2Br$)
(3) 4,6-O-ethylidene-2,3-di-O-dichloroacetyl-β-D-glucopyranose (in formula (2), R2 =—$COCHCl_2$)
(4) 4,6-O-ethylidene-2,3-di-O-dibromoacetyl-β-D-glucopyranose(in formula (2), $R_2$=—$COCHBr_2$)
(5) 4,6-O-ethylidene-2,3-di-0-trichloroacetyl-β-D-glucopyranose (in formula (2), $R_2$=—$COCCl_3$)
(6) 4,6-O-ethylidene-2,3-di-0-tribromoacetyl-β-D-glucopyranose(in formula (2), $R_2$=—$COCBr_3$)
(7) 4,6-0-ethylidene-2,3-di-O-β,β,β-trichloro-ethoxycarbonyl-β-D-glucopyranose (in formula (2), $R_2$=—$COOCH_2CCl_3$)
(8) 4,6-O-ethylidene-2,3-di-O-β,β,β-tribromo-ethoxycarbonyl-β-D-glucopyranose (in formula (2), $R_2$=—$COOCH_2CBr_3$).

The reaction of the compound (1) and the compound (2) provides the functional group-protected etoposide derivative of formula (3) in which the protective groups correspond to the protective groups contained in the starting compounds of formulas (1) and (2), respectively. Specific examples of the etoposide derivative of formula (3) include the following:

(1) 4'-chloroacetyl-4'-demethyl-epipodophyllotoxin-β-D-2, 3-di-O-chloroacetyl-4, 6-O-ethylidene-glucoside (in formula (3), $R_1$, $R_2$ =—$COCH_2Cl$)

(2) 4'-dichloroacetyl-4'-demethyl-epipodophyllotoxin-β-D-2,3-di-O-dichloroacetyl-4,6-O-ethylidene-glucoside (in formula (3), $R_1$, $R_2$=—$COCHCl_2$)

(3) 4'-trichloroacetyl-4'-demethyl-epipodophyllotoxin-β-D-2,3-di-O-trichloroacetyl-4,6-O-ethylidene-glucoside (in formula (3), $R_1$, $R_2$=—$COCCl_3$)

(4) 4'-bromoacetyl-4'-demethyl-epipodophyllotoxin-β-D-2, 3-di-O-bromoacetyl-4,6-O-ethylidene-glucoside (in formula (3), $R_1$, $R_2$=—$COCH_2Br$)

(5) 4'-chloroacetyl-4'-demethyl-epipodophyllotoxin-β-D-2, 3-di-O-β,β,β-trichloroethoxycarbonyl-4,6-O-ethylidene-glucoside (in formula (3), $R_1$ =—$COCH_2Cl$, $R_2$=—$COOCH_2CCl_3$).

Next, the present invention will be described in more detail with reference to the examples below.

Example 1

While stirring, 1.67 g of Compound (3) of formula (2) (wherein $R_2$=$COCHCl_2$), 0.5 ml of acetonitrile and 2.5 ml of toluene were mixed with each other. The resulting mixture was cooled to −10° C. or below. To the mixture was added 0.55 g of boron trifluoride diethyl ether complex. Then 1.00 g of Compound (3) of formula (1) (wherein $R_1$=$COCHCl_2$) was added to the reaction mixture. While maintaining the reaction temperature below −10° C, the reaction was continued for 30 minutes. The reaction was terminated by adding 0.46 g of pyridine to the system. After 20 ml of ethyl acetate and 20 ml of water were added to the reaction mixture, the mixture was stirred followed by fractionation. By repetition of water washing twice, the organic layer containing Compound (2) of formula (3) (wherein $R_1$, $R_2$=$COCHCl_2$) was obtained. High performance liquid chromatography analysis reveals that the rate of the by-produced dimer was 1.31% based on the objective Compound (2) of formula (3).

Example 2

The same procedures as in Example 1 were carried out except that 0.5 ml of acetone was employed in place of 0.5 ml of acetonitrile in Example 1. The same analysis reveals that the rate of the by-produced dimer was 6.96% based on the objective Compound (2) of formula (3).

Example 3

The same procedures as in Example 1 were carried out except that 0.5 ml of ethyl acetate was employed in place of 0.5 ml of acetonitrile in Example 1. The same analysis reveals that the rate of the by-produced dimer was 4.13% based on the objective Compound (2) of formula (3).

Example 4

The same procedures as in Example 1 were carried out except that 0.5 ml of ethyl acetate was employed singly in place of 0.5 ml of acetonitrile and 2.5 ml of toluene in Example 1. The same analysis reveals that the rate of the by-produced dimer was 11.42% based on the objective Compound (2) of formula (3).

Comparative Example 1

The same procedures as in Example 1 were carried out except that 10 ml (10-fold parts by weight based on the compound of formula (1)) of acetone alone was employed singly in place of 0.5 ml of acetonitrile and 2.5 ml of toluene in Example 1. The same analysis reveals that the rate of the by-produced dimer was 110.0% based on the objective Compound (2) of formula (3).

Comparative Example 2

The same procedures as in Example 1 were carried out except that 10 ml (10-fold parts by weight based on the compound of formula (1)) of ethyl acetate alone was employed singly in place of 0.5 ml of acetonitrile and 2.5 ml of toluene in Example 1. The same analysis reveals that the rate of the by-produced dimer was 43.99% based on the objective Compound (2) of formula (3).

Example 5

While stirring, 1.67 g of Compound (3) of formula (2) (wherein $R_2$=$COCHCl_2$), 0.5 ml of acetonitrile and 2.5 ml of toluene were mixed with each other. Furthermore, 0.5 ml of ethylene glycol dimethyl ether was added thereto. The resulting mixture was cooled to −10° C. or below. To the mixture was added 0.83 g of boron trifluoride diethyl ether complex. Then 1.00 g of Compound (3) of formula (1) (wherein $R_1$=$COCHCl_2$) was added to the reaction mixture. While maintaining the reaction temperature below −10° C., the reaction was continued for 3 hours. The reaction was terminated by adding 0.7 g of pyridine to the system. After 20 ml of ethyl acetate and 20 ml of water were added to the reaction mixture, the mixture was stirred followed by fractionation. By repetition of water washing twice, the organic layer containing Compound (2) of formula (3) (wherein $R_1$, $R_2$=$COCHCl_2$) was obtained. After 3 ml of methanol and 1.5 g of ammonium acetate were added to the organic layer, the mixture was stirred at 40° C. for 8 hours to obtain the reaction solution containing the etoposide. High performance liquid chromatography analysis of the reaction solution reveals that the reaction solution contained 1.11 g of etoposide. Yield, 96.9%.

The α-glucoside was 1.65% (per unit area) based on the etoposide.

The reaction solution above was heated to 40° C. Water was then added thereto to crystallize followed by cooling below 25° C. After washing with water and filtering, crude etoposide was obtained. The thus obtained etoposide showed a purity of about 97.7%, whereas the contents of the α-glucoside and the dimer were both less than 1%. The halogen compound content was 80 ppb or less.

According to the present invention described in detail hereinabove, etoposides which are considered to be useful as carcinostatic medicines can be obtained in a high purity, without accompanied by undesirable by-products and without using any harmful halogen type solvents.

What is claimed is:

1. A process for producing an etoposide or derivative thereof which comprises reacting a protected 4'-demethyl-4-epipodophyllotoxin of formula (1):

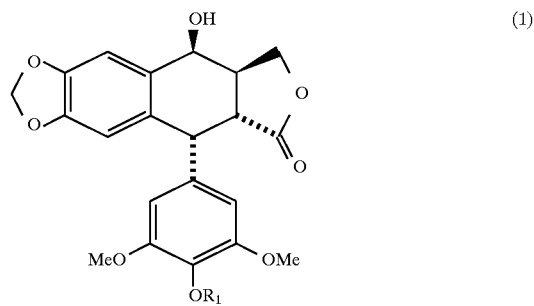

wherein $R_1$ is a protective group for hydroxy, with a protected glucose derivative of formula (2):

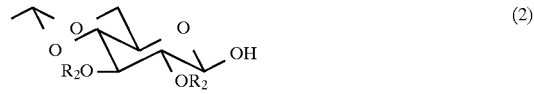

wherein $R_2$ is a protective group for hydroxy, in a non-halogen type organic solvent, in the presence of a non-halogen type aliphatic solvent in a 0.1 to 7-fold part by volume based on 1 part by weight of the etoposide or derivative thereof of formula (1) and a dehydration condensing catalyst, to obtain a protected etoposide of formula (3):

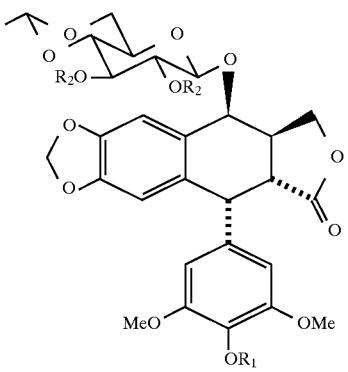

(3)

wherein $R_1$ and $R_2$ are as defined above, and optionally removing the protective group(s) from the protected etoposide.

2. A process for producing an etoposide or derivative thereof according to claim 1, wherein an ether is co-present in the reaction system.

3. A process for producing an etoposide or derivative thereof according to claim 1, wherein a boron trifluoride di-lower alkyl ether complex or a tri($C_1$—$C_4$ alkyl) silyltrifluoromethanesulfonate is employed as the catalyst.

4. A process for producing an etoposide or derivative thereof according to claim 2, wherein the ether is a mono or polyether containing 1 to 5 ether groups and 2 to 6 linear or cyclic hydrocarbon groups having 1 to 6 carbon atoms.

5. A process for producing an etoposide or derivative thereof according to claim 4, wherein the mono or polyether is represented by formula (4):

$$R_3-O-(R_4-O)_n-R_5 \quad (4)$$

wherein n is an integer of 0 to 4; each of $R_3$ and $R_5$ independently is an alkyl group having 1 to 4 carbon atoms; and $R_4$ is a linear or branched alkylene group having 2 to 4 carbon atoms.

6. A process for producing an etoposide or derivative thereof according to claim 1, wherein as the non-halogen type solvent, acetonitrile alone or a solvent mixture of acetonitrile and an aromatic solvent is employed.

7. A process for producing an etoposide or derivative thereof which comprises reacting a protected 4'-demethyl-4-epipodophyllotoxin of formula (1):

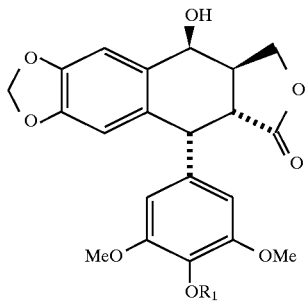

(1)

wherein $R_1$ is a protective group for hydroxy, with a protected glucose derivative of formula (2):

(2)

wherein $R_2$ is a protective group for hydroxy, in a solvent mixture of a non-halogen type aliphatic solvent and a non-halogen type aromatic solvent in the presence of a dehydration condensing catalyst, to obtain a protected etoposide of formula (3):

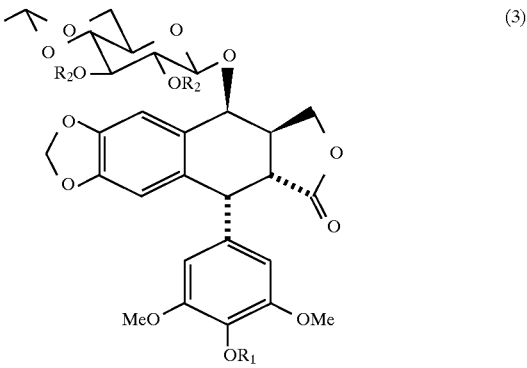

wherein $R_1$ and $R_2$ are as defined above, and optionally removing the protective group(s) from the protected etoposide.

8. A process for producing an etoposide or derivative thereof according to claim 7, wherein the non-halogen type aliphatic solvent is selected from the group consisting of a nitrile compound, a ketone compound and an ester compound.

9. A process for producing an etoposide or derivative thereof according to claim 8, wherein used is as the non-halogen type aliphatic solvent a nitrile compound of which aliphatic hydrocarbon group is selected from the group consisting of an alkyl group having 1 to 3 carbon atoms and an alkylene group having 1 to 3 carbon atoms; a ketone compound of which aliphatic hydrocarbon groups at the both sides therein are selected from the group consisting of an alkyl group having 1 to 5 carbon atoms and an alkylene group having 1 to 5 carbon atoms; and an ester compound which is an ester of acetic acid or propionic acid and an alcohol having 1 to 4 carbon atoms.

10. A process for producing an etoposide or derivative thereof according to claim 8, wherein the non-halogen type aromatic solvent is benzene or a benzene substituted with 1 to 3 substituents selected from the group consisting of an alkyl group having 1 to 4 carbon atoms and nitro.

11. A process for producing an etoposide or derivative thereof according to claim 7, wherein an amount of the non-halogen type aliphatic solvent used is in the range of 0.1 to 4-fold parts by volume based on 1 part by weight of the compound of formula (1) and the total amount of the solvent mixture is in the range of 1 to 10-fold parts by volume based on 1 part by weight of the compound of formula (1).

12. A process for producing an etoposide or derivative thereof according to claim 11, wherein the non-halogen type aliphatic solvent is selected from the group consisting of acetonitrile, propionitrile, acetone, methyl ethyl ketone, methyl isobutyl ketone, ethyl acetate and isopropyl acetate; the non-halogen type aromatic solvent is selected from the group consisting of benzene, toluene, xylene, ethylbenzene, nitrobenzene and nitrotoluene; and the dehydration condensing catalyst is a boron trifluoride di-alkyl ether having 1 to 4 carbon atoms and is employed in an amount ranging from 1 to 15 equivalents to the 4'-demethyl-4-etoposide of formula (1).

13. A process for producing an etoposide or derivative thereof according to claim 12 wherein the non-halogen type aliphatic solvent is a solvent mixture of acetonitrile and benzene, toluene or xylene, an amount of acetonitrile used being in the range of 0.3 to 3 parts by volume based on 1 part by weight of the compound of formula (1), a total amount of the solvent mixture being in the range of 2 to 6 parts by volume based on 1 part by weight of the compound of formula (1), and an amount of the boron trifluoride di-alkyl ether having 1 to 4 carbon atoms used as a catalyst is in the range of 1 to 6 equivalents to the compound of formula (1).

14. A process for producing etoposide or derivative thereof which comprises reacting a protected 4'-demethyl-4-epipodophyllotoxin of the formula (1)

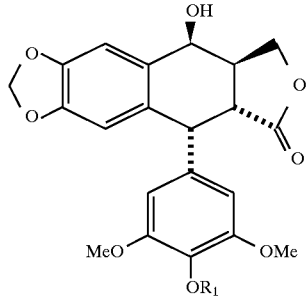
(1)

wherein $R_1$ is a protective group for hydroxy, with a protected glucose derivative of formula (2).

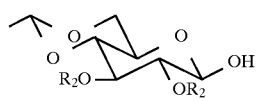
(2)

wherein $R_2$ is a protective gruop for hydroxy, in a non-halogen type aliphatic solvent in the presence of a dehydration condensing catalyst, to obtain a protected etoposide of formula (3):

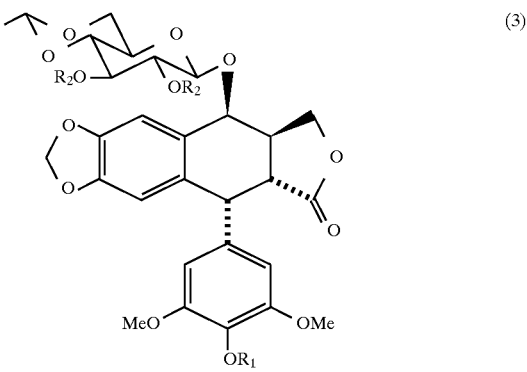
(3)

wherein $R_1$ and $R_2$ are as defined above, and optionally removing the protective groups(s) from the protected etoposide, wherein the non-halogen type aliphatic solvent is a nitrile compound at an amount in the range of 1 to 10-fold parts by volume based on 1 part by weight of the compound of formula (1).

* * * * *